United States Patent [19]

Becker et al.

[11] 4,063,891
[45] Dec. 20, 1977

[54] METHOD FOR DETERMINING THE INORGANIC CARBON CONTENT OF AQUEOUS LIQUIDS

[75] Inventors: Wolf-Jürgen Becker, Leverkusen; Alois Rüse, Oberursel, both of Germany

[73] Assignees: Bayer Aktiengesellschaft, Leverkusen; Hartmann & Braun Aktiengesellschaft, Frankfurt, both of Germany

[21] Appl. No.: 706,100

[22] Filed: July 16, 1976

[30] Foreign Application Priority Data

July 31, 1975 Germany .............................. 2534257

[51] Int. Cl.² .............................................. G01N 33/18
[52] U.S. Cl. .............................. 23/230 PC; 23/230 R; 23/253 PC; 23/254 R

[58] Field of Search ........ 23/230 PC, 253 PC, 230 R, 23/253 R, 232 R, 254 R

[56] References Cited

U.S. PATENT DOCUMENTS

| 3,672,841 | 6/1972 | Freeman, Jr. et al. .......... 23/230 PC |
| 3,840,341 | 10/1974 | Rogers .............................. 23/230 PC |

*Primary Examiner*—R.E. Serwin
*Attorney, Agent, or Firm*—Burgess, Dinklage & Sprung

[57] ABSTRACT

In a method for determining the inorganic carbon content of aqueous liquids, the liquid sample together with a carbon dioxide free carrier gas is injected vertically from top to bottom in to a heated reaction chamber. The reaction chamber is filled with liquid phosphoric acid. The carbon dioxide generated in the reaction of the sample with the phosphoric acid is fed to a $CO_2$ analyser. The reaction chamber is preferably heated to a temperature of approximately 140° C.

7 Claims, 1 Drawing Figure

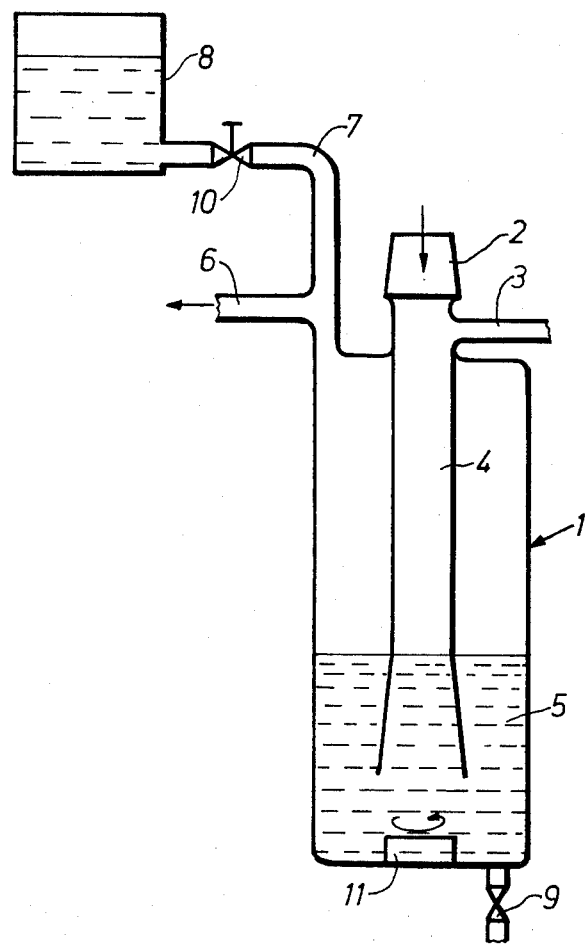

METHOD FOR DETERMINING THE INORGANIC CARBON CONTENT OF AQUEOUS LIQUIDS

The invention relates to a method for determining the inorganic carbon content of aqueous liquids, in which a sample of the liquid to be analysed is placed in a heated reaction chamber together with a carbon dioxide-free carrier gas, is reacted there wih phosphoric acid to form carbon dioxide and water and the carbon dioxide generated is fed to a $CO_2$ analyser.

Methods and devices for the pyrolytic determination of the total carbon content (TC = total carbon) of aqueous liquids are described in German Offenlegungsschriften 2,261,456 and 2,261,449. The total carbon content is composed of the organic (TOC = total organic carbon) and the inorganic (TIC = total inorganic carbon) carbon content. In many surface waters, domestic waste water etc., the inorganic carbon content (carbonate hardness) is often of the same order of magnitude as the organic carbon content. It is therefore necessary to determine both values (TOC and TIC) in analysing waste water.

German Auslegeschrift 1,598,361 describes a method for determining the inorganic carbon content of aqueous dispersions. A specific quantity of the liquid to be analysed is injected into a heated zone containing a body having an acid surface, which is reactive towards carbonate. A carbon dioxide-free carrier gas flow transports the gas mixture formed to a carbon dioxide analyser connected downstream. The heating zone is at a temperature above 100° C. However the temperature should not be so high that the organic components of the liquid decompose. The reactive body having an acid surface consists of quartz chips, coated with 85% phosphoric acid. A manual device working according to this method is commerically available.

However, this device displays relatively large spreads of the measurement values for the injection of a liquid of constant concentration. The reproducibility of the measurement values leaves much to be desired. The reason for the poor reproducibility can be seen in the fact that the liquid samples are sprayed repeatedly onto the same portion of the reactive body. In this way this place becomes deprived of the reactive substance (phosphoric acid). The required quantity of the reactive substance cannot be supplied from the other parts of the body. A further disadvantage of this device is that part of the sample liquid injected reaches the walls of the reaction chamber. The water evaporates there immediately because of the high temperature prevailing in the reaction chamber and the dissolved carbonates are precipitated in solid form, so that they are lost to the analysis.

The object of the invention is to improve the known method for the determination of the carbonate hardness in respect of accuracy and reproducibility. A measurement accuracy and reproducibility of a few percent (relative to the measurement value) is desired. An important step in this direction was the recognition that the reaction agent should be supplied in excess in the reaction with the injected liquid sample and in addition that the sample should reach the reaction agent as quickly as possible.

According to the invention, there is provided a method for determining the inorganic carbon content of aqueous liquids, wherein a liquid sample to be analysed is injected vertically downwards into a reaction chamber containing liquid phosphoric acid, into which is also fed a carbon dioxide-free carrier gas, the sample reacting with the phosphoric acid to form carbon dioxide and water and the carbon dioxide generated is fed to a carbon dioxide analyser. Preferably pure 85% phosphoric acid should be used as the reaction agent and the reaction chamber should be heated to a temperature of approximately 140° C. According to a preferred embodiment of the invention, the phosphoric acid in the reaction chamber is renewed continously or completely in a single process or in a plurality of successive processes by stages.

It has been shown that the reaction can be affected by the cool carrier gas. For this reason it is appropriate to heat the carrier gas to the temperature prevailing in the chamber before entry into the reaction chamber.

By this method a measurement accuracy of approximately 2% is achieved. The reduction of concentration of the reactive substance in the zone of encountering the liquid sample to be analysed can no longer take place, since the phosphoric acid is present in excess. In addition it has been possible to improve substantially the service life and long term stability relative to devices of the prior art.

An embodiment of the invention is shown in the accompanying drawing and described in more detail below.

The dosing of the aqueous liquid sample to be analysed into a vertical reaction chamber 1 takes place through a connecting pipe 2. In manual dosing, the connecting pipe 2 is closed by a rubber intercepting cap. In automatic dosing the connecting pipe 2 opens onto a smooth surface on which a dosing valve is seated. A suitable dosing valve is described in German Offenlegungsschrift No. 2,261,449.

An electric tube furnace (not shown), is located above the reaction chamber 1 which generates a temperature of approximately 140° C in the reaction chamber. By means of a metal tube between the heating furnace inner wall and the reaction chamber 1 the whole chamber is at approximately the same temperature. The metal tube (e.g. copper) conducts the heat to the projecting upper side of the chamber. The reaction agent in the reaction chamber 1 should as far as possible have the same temperature at all points. To prevent the reaction zone cooling down as a result of the feeding of the carbon dioxide-free carrier gas, the carrier gas is passed in a separate tube through the heating zone of the furnace in which it is heated and then passed through the inlet 3 at the connecting pipe 2 into the interior of the reaction chamber 1. By means of the guide pipe 4 the preheated carrier gas is passed through the 85% liquid phosphoric acid serving as the reaction agent.

As described above, the sample to be analysed is introduced through the connecting pipe 2 and passes together with the carrier gas through the guide pipe 4 into the reaction agent 5. The guide pipe 4 is immersed in the phosphoric acid 5 by more than half the level height of the acid. The effect of this is that the liquid sample to be analysed takes the longest possible path through the reaction agent 5, without excessively large dead volumes arising because of this.

The carrier gas and the carbon dioxide formed from the inorganic carbon compounds (carbonates) is forced through the chamber 1 by the over-pressure and fed through the outlet pipe 6 to a carbon dioxide analyser. There the carbon dioxide content is quantitatively determined. It corresponds to the content of carbonates and thus to the quantity of inorganically bonded carbon which is being sought.

In the case of a high salt content of the liquid to be analysed it is necessary to renew the reaction agent at regular intervals. To this end, the reaction vessel is connected to a further connecting pipe 7, which leads to a storage container 8 for pure 85% phosphoric acid. The "used" phosphoric acid 5 in the reaction chamber 1 can be discharged through a normally closed outlet 9. To renew the phosphoric acid, a tap 10 in the pipe 7 to the phosphoric acid storage container 8 has merely to be opened. It is also possible to renew continuously the phosphoric acid 5 in the reaction chamber 1. The connection pipe 7 to the storage container 8 for the phosphoric acid then consists of a capillary tube, through which continously new phosphoric acid flows in to the reaction chamber 1. The same quantity of phosphoric acid must then be drawn off at the outlet 9.

To homogenise the reaction agent and to avoid depletion in the reaction zone, a magnetic agitator 11 is provided in the floor of the reaction chamber 1. It is set in motion by a rotating field device (not shown).

What we claim is:

1. A method for determining the inorganic carbon content of aqueous liquids, wherein a liquid sample to be analysed is injected vertically downwards into a reaction chamber containing liquid phosphoric acid, into which is also fed a carbon dioxide-free carrier gas, the sample reacting with the phosphoric acid to form carbon dioxide and water and the carbon dioxide generated is fed to a carbon dioxide analyser.

2. A method as claimed in Claim 1, wherein the phosphoric acid is pure 85% phosphoric acid and a temperature of approximately 140° C is maintained in the reaction chamber.

3. A method as claimed in Claim 1, wherein the phosphoric acid is renewed continuously.

4. A method as claimed in Claim 1, wherein the phosphoric acid is periodically entirely replaced.

5. A method as claimed in Claim 1, wherein a portion of the phosphoric acid is periodically replaced.

6. A method as claimed in claim 1, wherein the carrier gas is heated to the temperature prevailing in the reaction chamber before it is fed into the reaction chamber.

7. A method as claimed in claim 2, wherein the carrier gas is heated to the temperature prevailing in the reaction chamber before it is fed into the reaction chamber.

* * * * *